United States Patent [19]

Yasushi et al.

[11] Patent Number: 4,645,830
[45] Date of Patent: Feb. 24, 1987

[54] STABLE COMPOSITION OF INTERLEUKIN-2 AND ALBUMIN

[75] Inventors: Mikura Yasushi; Asada Kensuke, both of Suita; Toguchi Hajime, Nishinomiya, all of Japan

[73] Assignee: Takeda Chemical Industries, Osaka, Japan

[21] Appl. No.: 720,754

[22] Filed: Apr. 8, 1985

[30] Foreign Application Priority Data

Apr. 9, 1984 [JP] Japan ................................. 59-71568
Jan. 25, 1985 [JP] Japan ................................. 60-13226
Feb. 25, 1985 [JP] Japan ................................. 60-37184

[51] Int. Cl.[4] ...................... A61K 45/02; A61K 37/02
[52] U.S. Cl. ................................. 530/351; 435/68; 435/948; 514/2; 514/8; 514/12; 514/21; 530/828
[58] Field of Search ............. 260/112 R, 121; 435/68, 435/172.3, 240, 241, 948; 514/2, 8, 12, 21; 530/351, 828

[56] References Cited

U.S. PATENT DOCUMENTS

| | | | |
|---|---|---|---|
| 4,401,756 | 8/1983 | Gillis | 435/68 |
| 4,404,280 | 9/1983 | Gillis | 435/68 |
| 4,462,940 | 7/1984 | Hanisch et al. | 260/112 R |
| 4,490,289 | 12/1984 | Stern | 260/112 R |
| 4,508,833 | 4/1985 | Sonneborn et al. | 260/112 R X |
| 4,518,584 | 5/1985 | Mark et al. | 260/112 R X |
| 4,530,787 | 7/1985 | Shaked et al. | 530/351 |
| 4,572,798 | 2/1986 | Koths et al. | 530/351 |
| 4,578,335 | 3/1986 | Urdal et al. | 435/68 |
| 4,604,377 | 8/1986 | Fernandes et al. | 530/351 X |

OTHER PUBLICATIONS

Rubin et al, PNAS, 77, No. 10, 5928-5932 (1980).
Nature, 302, 305-310 (1983), Taniguchi et al.

*Primary Examiner*—Howard E. Schain
*Attorney, Agent, or Firm*—David G. Conlin; Ronald I. Eisenstein

[57] ABSTRACT

The present invention provides an interleukin-2 composition which comprises human serum albumin, a reducing compound or a combination thereof and is adjusted as showing pH of 3 to 6 as a solution. The composition of the present invention is characterized in that interleukin-2 activity is minimized during storage and in the processes of freezing and lyophilization.

16 Claims, No Drawings

STABLE COMPOSITION OF INTERLEUKIN-2 AND ALBUMIN

This invention relates to an interleukin 2 composition.

Interleukin-2 (hereinafter sometimes referred to by the abbreviation IL-2) is a protein capable of functioning as a growth factor for T cells and natural killer cells which are considered to play an important role in in vivo immunomodulation and directly or indirectly contribute to elimination of cancer or recovery from or improvement in the immunocompromised state [Nature, 302, 305–310 (1983)]. As such, IL-2 is expected to be usable as a novel type of anticancer agent or a therapeutic agent for imminodeficiency.

It has been found that IL-2 is unstable and easily loses its activity during the process of freezing or lyophilization and during storage following lyophilization, in particular in the step of drying in lyophilization. In addition, solutions obtained upon redissolution of lyophilized IL-2 preparations generally become turbid. These factors, among others, adversely for the use of IL-2 for therapeutic purposes.

In accordance with the present invention, there is provided a stable IL-2 composition which comprises, in addition to IL-2, either human serum albumin, a reducing compound or a combination thereof and which, as a solution, is adjusted to pH of 3 to 6.

In the practice of the invention, the IL-2 may be of any mammal but is preferably of human origin. The IL-2 may also be a natural one or a product of recombinant DNA technology, although the latter is preferred. Mixtures of IL-2 may also be used. IL-2 is generally used in the form of an aqueous solution.

Preferred examples of IL-2 are non-glycosylated human IL-2 species produced by genetic engineering and having the sequence:

$$
\begin{aligned}
&1\\
&X-\text{Ala Pro Thr Ser Ser Ser Thr Lys Lys Thr Gln Leu}\\
&20\\
&\text{Gln Leu Glu His Leu Leu Leu Asp Leu Gln Met Ile Leu}\\
&\text{Asn Gly Ile Asn Asn Tyr Lys Asn Pro Lys Leu Thr Arg}\\
&40\\
&\text{Met Leu Thr Phe Lys Phe Try Met Pro Lys Lys Ala Thr}\\
&60\\
&\text{Glu Leu Lys His Leu Gln Cys Leu Glu Glu Glu Leu Lys}\\
&\text{Pro Leu Glu Glu Val Leu Asn Leu Ala Gln Ser Lys Asn}\\
&80\\
&\text{Phe His Leu Arg Pro Arg Asp Leu Ile Ser Asn Ile Asn}\\
&100\\
&\text{Val Ile Val Leu Glu Leu Lys Gly Ser Glu Thr Thr Phe}\\
&\text{Met Cys Glu Tyr Ala Asp Glu Thr Ala Thr Ile Val Glu}\\
&120\\
&\text{Phe Leu Asn Arg Trp Ile Thr Phe Cys Gln Ser Ile Ile}\\
&133\\
&\text{Ser Thr Leu Thr}
\end{aligned}
\tag{I}
$$

wherein X is Met or hydrogen.

In the above formula (I), each amino acid residue is represented by the abbreviation according to the IUPAC-IUB Commission on Biochemical Nomenclature.

The IL-2 component of the composition desirably has a specific activity of 20,000 to 80,000 units/mg and is advantageously used in the form of an aqueous IL-2 solution having an activity of 1 to 80,000 units/ml, preferably 10 to 50,000 units/ml, more preferably 50 to 5,000 units/ml. The aqueous IL-2 solution used as the raw material in the practice of the invention is preferably free from salts such as sodium chloride. When said solution is contaminated with a salt in the IL-2 purification process, for instance, it is preferable to remove the salt by ultrafiltration, for instance, prior to use thereof.

The human serum albumin component of the composition (hereinafter referred to be the abbreviation HSA) may be of any grade. For clinical application of the composition, however, said HSA is preferably of a quality allowing the use by parenteral administration. Particularly useful is HSA fractionated and purified by Cohn's 6th method of ethanol fractionation with healthy human plasma as the starting material [J. Am. Chem. Soc. 68, 459–475 (1946)]. Said HSA may also contain acetyltryptophan sodium or sodium caprylate as a stabilizer. The concentration of HSA is preferably 0.1 to 50 mg, more preferably 0.5 to 20 mg, per milliliter of the aqueous IL-2 solution having an IL-2 concentration within the range mentioned above.

The reducing compound component is preferably a physiologically acceptable reducing compound and thus includes sulfur-containing reducing compounds such as glutathione (reduced form; hereinafter simply glutathione), thioctic acid, N-acetylcysteine, N-acetylhomocysteine, thiodiglycol, thioethanolamine, monothioglycerol, dithiothreitol and thioalkanoic acids containing 1–7 carbon atoms (e.g. thioglycolic acid, thiomalic acid), and ascorbic acid and salts thereof, or mixtures thereof. Preferred are acidic compound such as glutathione, thioctic acid, N-acethylcysteine and ascorbic acid, and particularly preferred are glutathione and ascorbic acid.

The reducing compounds mentioned above may be used either alone or in combination of two or more.

These reducing compounds are used preferably in an amount of not less than 0.01 mg, more preferably 0.05 to 20 mg, per milliliter of the aqueous IL-2 solution having a concentration within the above-mentioned range.

HSA and the reducing compound mentioned above may be used both of them within the above-mentioned range or each of them alone, and HSA is preferably used.

The IL-2 composition according to the invention may further contain one or more substances selected from the group of amino acids, in particular monoamino aliphatic amino acids and cyclic amino acids, such as glycine, glutamic acid, aspartic acid, alanine and proline, monosaccharides such as glucose and mannose, sugar alcohols such as sorbitol and mannitol, and physiologically acceptable salts and derivatives thereof. Among these auxiliary additives, glycine is particularly preferred.

The above auxiliary additives are preferably used in amounts of 10–100 mg for monosaccharides and sugar alcohols and 5–50 mg for amino acids per milliliter of the abovementioned aqueous IL-2 solution.

The IL-2 composition according to the invention may further contain an isotonizing agent such as sodium chloride, a buffer such as succinic acid, tartaric acid or citric acid, and/or a surfactant. However, as noted above, the IL-2 composition is preferably free of sodium chloride which affects the stability of IL-2 during lyophilization.

In order that the IL-2 composition according to the present invention gives a pH of 3 to 6, preferably 3 to 5.5, more preferably 3.5 to 4.5, said composition is adjusted to a pH within the range specified herein with an acidic reducing compound or an acidic amino acid such as glutamic acid when such compound is added, or, in cases when if further desired and when no acidic compound is contained, with a mineral acid such as hydrochloric acid or phosphoric acid, or a buffer of organic acid such as succinic acid, tartaric acid or citric acid.

The stability of the above IL-2 composition may be further increased by evacuating the space within containers for the IL-2 composition or filling said space with nitrogen.

The IL-2 composition according to the present invention preferably takes the form of an aqueous solution, frozen matter, lyophilizate or the like, preferably the form of a lyophilizate.

The composition according to the invention may be produced, for example in the following manner:

To an aqueous solution of IL-2 in a concentration of 1 to 80,000 units/ml, there is added HSA and/or reducing compound to a predetermined concentration, followed by pH adjustment in the manner mentioned above.

Monosaccharides, sugar alcohols and amino acids may also be added in the respective concentrations mentioned above. If desired, an isotonizing agent, a surfactant, and so forth may further be added. Also in case of adding such auxiliary additives, pH adjustment is performed in the manner mentioned above so that the final aqueous solution can have a pH within the above range. The IL-2 composition thus obtained may be used also as the raw material in producing a frozen matter or a lyophilizate in the manner mentioned below.

The frozen form of the IL-2 composition may be produced, for example, by freezing the above aqueous solution generally at $-80°$ to $-20°$ C. Said frozen composition is preferably stored at $-80°$ to $-10°$ C.

The lyophilizate form of the IL-2 composition may be produced, for example, by drying the above frozen composition under reduced pressure in the conventional manner or by freezing the above aqueous solution or an aqueous solution resulting from thawing the above frozen composition, in the same manner as above, following distribution thereof as desired, and then drying the resulting frozen composition under reduced pressure by the conventional method.

Furthermore, the IL-2 composition according to the present invention which is in the form of a solution may be produced by redissolving an lyophilizate containing IL-2, HSA and/or a reducing compound, a pH adjusting agent, etc. as produced by the method mentioned above in a solvent containing a monosaccharide, sugar alcohol, amino acid, etc. and pH-adjusted, for example, with hydrochloric acid, as desired.

In producing the lyophilized IL-2 composition according to the invention for use as an injectable preparation, it is preferable to combine the IL-2-containing aqueous solution with an additive-containing aqueous solution, each after separate sterile filtration, or purify a mixture of the IL-2-containing aqueous solution and an additive-containing aqueous solution by sterile filtration etc., then distribute the mixture aseptically into vials or the like and subject the mixture in vials or the like to the above-mentioned lyophilization treatment.

Similarly, when dissolving the lyophilizate in an aqueous solution containing an amino acid, monosaccharide or sugar alcohol, it is preferred that the aqueous solution is subjected to sterile filtration, then distributed into ampuls or the like and autoclaved prior to its use as the solvent.

Among those IL-2 compositions provided by the invention, the lyophilizate in the form of a stabilized IL-2 powder and may be used advantageously as a preparation for parenteral administration. In using as a preparation for injection, the lyophilizate is dissolved in 0.5–100 ml of distilled water, physiological saline, or in 0.5–100 ml of a solvent attached to the lyophilizate composition. When the lyophilizate is dissolved in a solvent, the solvent is preferably an aqueous solution of an amino acid such as glycine, a monosaccharide such as glucose or a sugar alcohol such as mannitol. The pH is adjusted as necessary, and the solution is administered intramuscularly or intravenously. Said composition may also be used in the form of preparations for administration into the oral and nasal cavity or to the eye or ear by using an appropriate carrier, excipient or diluent.

The IL-2 composition according to the present invention possesses several advantages. It minimizes the decrease in IL-2 activity normally accompanying storage, freezing and lyophilization. Furthermore, the solution obtained upon redissolution of the lyophilizate is clear and transparent and adsorption on container walls is effectively prevented. Compositions which contain an amino acid when lyophilized have also been found to have an improved appearance. Another advantage is that pain accompanying administration by injection is effectively alleviated, including monosaccharide-containing compositions. Finally, the IL-2 composition is low in toxicity and may be used for the same purposes and in the same manner as known IL-2 preparations.

The IL-2 activity data given in units (U) in the present specification were obtained in the following manner:

A IL-2-containing test sample was added to a suspension, in a medium, of a mouse cell line capable of growing in the IL-2 concentration-dependent manner. After incubation, the growth of said cell line was determined with the uptake of tritiated thymidine as an index. In assaying, a standard IL-2 (1 U/ml) was always used in parallel with the test sample and the activity in units (U) of the test sample was calculated from the activity ratio therebetween.

Specifically, an IL-2-dependent mouse cell line [NKC3; Hinuma et al., Biochemical and Biophysical Research Communications, 109, 363 (1982)] maintained by subculture in RPMI 1640 medium containing human IL-2-containing conditioned medium plus 20% FCS (fetal calf serum) at 37° C. in the presence of 5% $CO_2$ was used. The cells were washed twice with serum-free RPMI 1640 medium and resuspended in 20% FCS-added RPMI 1640 medium in a concentration of $6 \times 10^5$ cells/ml.

All IL-2-containing test samples were distributed, in 50 $\mu$l portions, into the first row of wells on a 96-well flat-bottomed microtiter plate (Nunc, Denmark), followed by serial doubling dilution to the 12th row using 50 $\mu$l of 20% FCS-added RPMI 1640 medium per well. Then, 50 $\mu$l of the above NKC3 cell suspension was added to each well. Incubation was conducted at 37° C. in the presence of 5% $CO_2$ for 24 hours, during which, after 20 hours of incubation, 1 $\mu$Ci of tritiated thymidine (Amersham, Great Britain) was added to each well.

Cells were recovered on a glass filter using a cell harvester (Flow, U.S.A.) and measured for tritiated thymidine uptake using a liquid scintillation counter. In parallel, the same procedure was followed with a standard IL-2 sample for measuring tritiated thymidine uptake.

Activity calculation in units (U) was performed by the profit method according to Journal of Immunology, 120, 2027 (1978), Thus, among a dilution series derived from a standard IL-2 sample (the culture supernatant after 48-hour incubation, at 37° C. in the presence of 5% $CO_2$, of a $5\times10^6$/ml suspension of human peripheral blood lymphocytes in 10% FCS added RPMI 1640 medium with 40 μg of concanavalin A and 15 ng/ml of 12-O-tetradecanoylphorbol-13-acetate added being defined as having an activity of 1 U/ml), the maximum uptake was taken as 100%, and the percentage uptake (%) for each dilution stage was calculated. The values obtained were plotted on a normal probability paper and the dilution factor corresponding to 50% uptake was determined graphically. For each IL-2-containing test sample, the dilution factor corresponding to 50% uptake was determined in the same manner.

The IL-2 concentration (U/ml) in the test sample was calculated using the formula:

$$\frac{\text{Dilution factor at which test samples shows 50\% uptake}}{\text{Dilution factor at which standard IL-2 sample shows 50\% uptake}}$$

The transformant *Escherichia coli* DH1/pTF4 disclosed hereinafter in the Reference Example has been deposited with the Fermentation Institute, Osaka under the deposit number IFO-14299 and, since April 6, 1984, with the Fermentation Research Institute (FRI), Agency of Industrial Science and Technology, Ministry of International Trade and Industry under the deposit number FERM BP-628.

EXAMPLES

The following working examples and reference example illustrate the invention in further detail. However, they are by no means limitative of the present invention.

The stock solution used in the working examples was the non-glycosylated human IL-2 protein solution obtained by the method described in the reference example.

EXAMPLE 1

To an aqueous solution (0.5 ml) containing 2,450 units of human IL-2 as prepared by dilution of the stock solution with distilled water for injection followed by sterile filtration, there was added a soluton (0.5 ml) containing 10 mg of glutathione or ascorbic acid after sterile filtration. The two aqueous solutions (each 1 ml) thus obtained (pH 3.4 and pH 3.5, respectively) were each placed in a vial, frozen at −40° C., and lyophilized. Thereafter, the free space in the vial was filled with gaseous $N_2$ and the vial was stoppered tightly.

The same amount of an aqueous solution free of glutathione or ascorbic acid and the same amount of an aqueous solution containing 25 mg of mannitol, which is in frequent use in lyophilized preparations, in place of glutathione or ascorbic acid were used as controls and lyophilized in the same manner.

These lyophilizates were each redissolved in 1 ml of distilled water for injection and the solutions were examined for solubility (clarity) and potency. As for the potency, the potency of the aqueous solution prior to lyophilization was taken as 100% and the residual percentage was calculated. As the results shown in Table 1 indicate, the IL-2 compositions according to the invention were significantly superior both in solubility and residual potency to the controls.

TABLE 1

| Additive (mg) | Solubility | Residual potency |
|---|---|---|
| None | Turbid | 47% |
| Mannitol (25) | Turbid | 58% |
| Glutathione (10) | Clear | 97% |
| Ascorbic acid (10) | Clear | 100% |

EXAMPLE 2

To an aqueous solution (0.5 ml) containing 7,680 units of human IL-2 as prepared by dilution of the stock solution with distilled water for injection followed by sterile filtration, there was added a solution (0.5 ml) containing 2 mg of glutathione or ascorbic acid after sterile filtration. The two aqueous solution (each 1 ml) thus obtained (pH 3.6 and pH 3.7, respectively) were lyophilized in the same manner as in Example 1 and the lyophilizates were examined for solubility directly after manufacture and solubility and residual potency after storage at 25° C. for 1 month.

The results obtained are shown in Table 2.

TABLE 2

| Additive (mg) | Directly after manufacture | After 1 month at 25° C. Solubility | Potency |
|---|---|---|---|
| Glutathione (2) | Clear | Clear | 99% |
| Ascorbic acid (2) | Clear | Clear | 90% |

EXAMPLE 3

To an aqueous solution (0.5 ml) containing 7,680 units of human IL-2 as prepared by dilution of the stock solution with distilled water for injection followed by sterile filtration, there was added a solution (0.5 ml) containing 5 ml of HSA plus 2 mg of glutathione or ascorbic acid after sterile filtration. The two aqueous solutions (each 1 ml) thus obtained (pH 4.1 and pH 4.2, respectively), were lyophilized in the same manner as in Example 1 and the lyophilizates were examined for solubility and residual potency in the same manner as in Example 2.

The results obtained are shown in Table 3.

TABLE 3

| Additive (mg) | Directly after manufacture Solubility | After 1 month at 25° C. Solubility | Potency |
|---|---|---|---|
| Glutathione (2) plus HSA (5) | Clear | Clear | 104% |
| Ascorbic acid (2) plus HSA (5) | Clear | Clear | 101% |

EXAMPLE 4

To an aqueous solution (0.5 ml) containing 7,680 units of human IL-2 as prepared by dilution of the stock solution with distilled water for injection followed by sterile filtration, there was added a solution (0.5 ml) containing 5 mg of HSA, 9 mg of sodium chloride and 2 mg of glutathione or ascorbic acid after sterile filtration. The two aqueous solutions (each 1 ml) thus obtained (pH 4.1 and pH 4.2, respectively) were lyophilized in the same manner as in Example 1 and the lyophilizates were examined for solubility and residual potency in the same manner as in Example 2.

The results obtained are shown in Table 4.

TABLE 4

| Additive (mg) | Directly after manufacture Solubility | After 1 month at 25° C. Solubility | Potency |
|---|---|---|---|
| Glutathione (2) + HSA (5) + sodium chloride (9) | Clear | Clear | 85% |
| Ascorbic acid (2) + HSA (5) + sodium chloride (9) | Clear | Clear | 93% |

EXAMPLE 5

To an aqueous solution (0.5 ml) containing 7,680 units of human IL-2 as prepared by dilution of the stock solution with distilled water for injection followed by sterile filtration, there was added a solution (0.5 ml) containing 50 mg of mannitol and 2 mg of glutathione or ascorbic acid after sterile filtration. The two aqueous solutions (each 1 ml) thus obtained (pH 3.4 and pH 3.6, respectively) were lyophilized in the same manner as in Example 1 and the lyophilizates were examined for solubility and residual potency in the same manner as in Example 2.

The results obtained are shown in Table 5.

TABLE 5

| Additive (mg) | Directly after manufacture Solubility | After 1 month at 25° C. Solubility | Potency |
|---|---|---|---|
| Glutathione (2) + mannitol (50) | Clear | Clear* | 114% |
| Ascorbic acid (2) + mannitol (50) | Clear | Clear | 95% |

*Data after storage at 25° C. for 6 days.

EXAMPLE 6

To an aqueous solution (0.5 ml) containing 23,350 units of human IL-2 as prepared by dilution of the stock solution with distilled water for injection followed by sterile filtration, there was added an aqueous solution (0.5 ml) containing 5 mg of glutathione and 23 mg of glycine after sterile filtration. The aqueous solution (1 ml) thus obtained (pH 3.7) was lyophilized in the same manner as in Example 1 and the lyophilizate was examined for solubility and residual potency directly after manufacture and after storage at 40° C. for 3 weeks in the same manner as in Example 1.

The results obtained are shown in Table 6.

TABLE 6

| Additive (mg) | Directly after manufacture Solubility | Potency | After 1 month at 40° C. Solubility | Potency |
|---|---|---|---|---|
| Glutathione (2) + glycine (23) | Clear | 95.1% | Clear | 107.1% |

EXAMPLE 7

To an aqueous solution (0.5 ml) containing 1,790 or 130 units of human IL-2 as prepared by dilution of the stock solution with distilled water for injection followed by sterile filtration, there was added an aqueous solution (0.5 ml) containing 2 mg of glutathione, 5 mg of HSA and 9 mg of sodium chloride after sterile filtration. The two aqueous solutions (each 1 ml) thus obtained (pH 3.9 both) were lyophilized in the same manner as in Example 1 and the lyophilizates were examined for solubility and residual potency directly after manufacture and after storage at 40° C. for 1 week in the same manner as in Example 1.

The results obtained are shown in Table 7.

TABLE 7

| Human IL-2 (units) | Additive (mg) | Directly after manufacture Solubility | Potency | After 1 week at 40° C. Solubility | Potency |
|---|---|---|---|---|---|
| 1,790 | Glutathione (2) + HSA (5) + sodium chloride (9) | Clear | 90% | Clear | 94% |
| 130 | Same as above | Clear | 94% | Clear | 89% |

EXAMPLE 8

To an aqueous solution (0.5 ml) containing 1,860 or 116 units of human IL-2 as prepared by dilution of the stock solution with distilled water for injection followed by sterile filtration, there was added an aqueous solution (0.5 ml) containing 2 mg of glutathione, 1 mg of HSA and 23 mg of glycine after sterile filtration. The two aqueous solutions (each 1 ml; pH 3.8 and pH 3.9, respectively) were lyophilized in the same manner as in Example 1 and the lyophilizates were examined for solubility and residual potency directly after manufacture and after storage at 40° C. for 1 week.

The results obtained are shown in Table 8.

TABLE 8

| Human IL-2 (units) | Additive (mg) | Directly after manufacture Solubility | Potency | After 1 week at 40° C. Solubility | Potency |
|---|---|---|---|---|---|
| 1,860 | Glutathione (2) + HSA (1) + glycine (23) | Clear | 90% | Clear | 98% |
| 116 | Same as above | Clear | 110% | Clear | 108% |

EXAMPLE 9

To an aqueous solution (0.5 ml) containing 17,600 units of human IL-2 as prepared by dilution of the stock solution with distilled water for injection followed by sterile filtration, there was added an aqueous solution (0.5 ml) containing 5 mg of HSA and having a pH of 4 (adjusted with hydrochloric acid) after sterile filtration or an aqueous solution (0.5 ml) containing 5 mg of HSA and 9 mg of sodium chloride and having a pH of 4 (adjusted with hydrochloric acid) after sterile filtration. The two aqueous solution (each 1 ml) thus obtained were each placed in a vial, frozen at −40° C., and lyophilized. Thereafter, the free space in the vial was filled with gaseous $N_2$ and the vial was stoppered tightly.

These lyophilizates were each redissolved in 1 ml of distilled water for injection directly after manufacture or after storage at 40° C. for 0.5 month and the solutions were examined for solubility (clarity) and potency. As for the potency, the potency of the aqueous solution prior to lyophilization was taken as 100% and the residual percentage was calculated based thereon. As the results shown in Table 9 indicate, the IL-2 compositions according to the invention were significantly superior in solubility and residual potency.

TABLE 9

| Additive (mg) | Directly after manufacture | | After 0.5 month at 40° C. | |
|---|---|---|---|---|
| | Solubility | Potency | Solubility | Potency |
| HSA (5) pH-adjusted with hydrochloric acid | Clear | 102.3% | Clear | 100.6% |
| HSA (5) + sodium chloride (9), pH-adjusted with hydrochloric acid | Clear | 113.6% | Clear | 110.2% |

EXAMPLE 10

To aqueous solutions (0.5 ml) containing 4,115 units/ml of human IL-2 as prepared by dilution of the stock solution with distilled water for injection followed by sterile filtration, there was added aqueous solutions (0.5 ml) containing 5 mg of HSA, 5 mg of HSA plus 9 mg of sodium chloride, 5 mg of HSA plus 23 of glycine, are 5 mg of HSA plus 50 mg of mannitol respectively, each having a pH of 4.0 (adjusted with hydrochloric acid) after sterile filtration. The four kinds of aqueous solutions (each 1 ml) thus obtained were each placed in a vial, frozen at −40° C., and lyophilized. Thereafter, the vial space was filled with gaseous N₂ and each vial was stoppered tightly. As controls, an aqueous solution of human IL-2 alone and various aqueous IL-2 solutions containing no pH adjusting agent were used in the same amount and lyophilized in the same manner as above.

These lyophilizates were examined for appearance and thereafter each redissolved in 1 ml of distilled water for injection, 0.9% physiological saline, 5% aqueous glucose solution, 5% aqueous sorbitol solution, and 5% aqueous mannitol solution, and the solutions were examined for pH and solubility (clarity).

As the results shown in Table 10 indicate, the IL-2 compositions according to the invention were significantly superior in solubility to the controls. In particular, the lyophilizate with HSA and glycine incorporated therein, which gave a pH of about 4, was superior in solubility.

TABLE 10

| | Human IL-2: 2058 units | | | | | |
|---|---|---|---|---|---|---|
| Additive (mg) | pH adjuster | Appearance | Solvent for redissolution | pH | Solubility | Remarks |
| None | None | Bad | Distd. water for injection | 5.6 | Turbid | Control |
| None | HCl* | " | Distd. water for injection | 4.2 | " | Control |
| HSA (5) | None | Good | Distd. water for injection | 5.8 | " | Control |
| " | HCl* | " | Distd. water for injection | 4.3 | Clear | |
| " | " | " | 0.9% physiol. saline | 4.3 | " | |
| " | " | " | 5% glucose aq. | 4.3 | " | |
| " | " | " | 5% sorbitol aq. | 4.3 | " | |
| " | " | " | 5% mannitol aq. | 4.3 | " | |
| " | " | " | 2.3% glycine aq. | 4.1 | " | Solvent adjusted to pH 4.1 |
| HSA (5) NaCl (9) | None | " | Distd. water for injection | 6.3 | Turbid | Control |
| HSA (5) NaCl (9) | HCl* | " | Distd. water for injection | 3.9 | Clear | |
| HSA (5) glycine (23) | None | " | Distd. water for injection | 6.3 | Turbid | Control |
| HSA (5) glycine (23) | HCl* | " | Distd. water for injection | 3.9 | Very clear | |
| HSA (5) mannitol (50) | None | " | Distd. water for injection | 5.6 | Turbid | Control |
| HSA (5) mannitol (50) | HCl* | " | Distd. water for injection | 4.1 | Clear | |

*Hydrochloric acid

EXAMPLE 11

Two aqueous solutions (each 1 ml) obtained by the procedure of Example 9 and deprived of bacteria by filtration and containing 1,620 and 128 units of human IL-2, respectively 5 mg of HSA and 23 mg of glycine and having a pH of 4.0 (adjusted with hydrochloric acid) were lyophilized in the same manner as in Example 9 and the lyophilizates were examined for solubility and residual potency directly after manufacture and after storage at 40° C. for 1, 2 and 4 weeks in the same manner as in Example 9.

The results obtained are shown in Table 11.

TABLE 11

| Human IL-2 (units) | Additive (mg) | pH | Directly after manufacture | | After 1 week at 40° C. | | After 2 weeks at 40° C. | | After 4 weeks at 40° C. | |
|---|---|---|---|---|---|---|---|---|---|---|
| | | | Solubility | Residual potency | Solubility | Residual potency | Solubility | Residual potency | Solubility | Residual potency |
| 1620 | HSA (5) + glycine (23) pH-adjusted with HCl | 4.0 | Very clear | 97.8% | Very clear | 101.2% | Very clear | 101.9% | Very clear | 98.8% |
| 128 | Same as | 4.0 | Very | 101.6% | Very | 100.8% | Very | 101.6% | Very | 100.0% |

TABLE 11-continued

| Human IL-2 (units) | Additive (mg) | Directly after manufacture |  | After 1 week at 40° C. |  | After 2 weeks at 40° C. |  | After 4 weeks at 40° C. |  |
|---|---|---|---|---|---|---|---|---|---|
|  |  | pH | Solubility | Residual potency | Solubility | Residual potency | Solubility | Residual potency | Solubility | Residual potency |
|  | above |  | clear |  | clear |  | clear |  | clear |  |

EXAMPLE 12

To aqueous solutions (0.5 ml) containing 2,450 units of human IL-2 as prepared by dilution of the stock solution with distilled water for injection followed by sterile filtration, there was added a distilled water for injection (0.5 ml), a sterile filtrate (0.5 ml) containing 10 mg of glutathione, glutathione disodium salt, ascorbic acid or sodium ascorbate and a sterile filtrate (0.5 ml) adjusted to acidic condition with hydrochloric acid and containing 10 mg of glutathion disodium salt or sodium ascorbate. The 7 kinds of aqueous solutions thus obtained were each placed in a vial, frozen at $-40°$ C., and lyophilized. Thereafter, the free space in the vial was filled with gaseous $N_2$ and the vial was stopped tightly. These lyophilizates were each redissolved in a 1 ml of distilled water for injection and the solutions were examined for pH and solubility (clarity). As the results shown in Table 12 indicate, the IL-2 compositions according to the invention were significantly superior in solubility to the controls.

TABLE 12

| Additive (mg) | pH adjuster | pH | Solubility | Remarks |
|---|---|---|---|---|
| None | None | 5.4 | Turbid | Control |
| Glutathione (10) | None | 3.4 | Clear |  |
| Glutathione disodium (10) | None | 9.2 | Turbid | Control |
| Glutathione disodium (10) | HCl* | 4.2 | Clear |  |
| Ascorbic acid (10) | None | 3.5 | Clear |  |
| Sodium ascorbate (10) | None | 6.5 | Some turbid | Control |
| Sodium ascorbate (10) | HCl* | 4.3 | Clear |  |

*hydrochloric acid

Reference Example

Production of Non-glycosylated human IL-2 protein solution (i) The human IL-2 gene-bearing transformant *Escherichia coli* (*E. coli*) DH1/pTF4 obtained in Example 3 of the specification for U.S. patent application No. 674,556 was inoculated into 50 ml of a liquid medium (pH 7.0) containing 1% Bacto-tryptone (Difco Laboratories, U.S.A.), 0.5% Bacto yeast extract (Difco Laboratories, U.S.A.), 0.5% sodium chloride and 7 μg/ml tetracycline in a 250-ml erlenmeyer flask, followed by incubation at 37° C. overnight in the manner of rolling shake culture. The culture fluid was transferred to a 5-liter jar fermenter containing 2.5 liters of M9 medium containing 0.5% casamino acids, 0.5% glucose and 7 μg/ml tetracycline, followed by 4 hours of incubation at 37° C. with aeration and stirring, then addition of 3-β-indolylacrylic acid (25 μg/ml) and further 4 hours of incubation under the same conditions. The thus-obtained culture fluid (2.5 liters) was subjected to centrifugation and the cells collected were frozen at $-80°$ C. and stored.

(ii) The cells obtained in the above (i) and stored in the frozen state (37.5 g) were suspended uniformly in 500 ml of an extractant (pH 7.0) containing 7M guanidine hydrochloride and 0.1M Tris.HCl, and the suspension was stirred at 4° C. for 1 hour. The resultant lysate solution was centrifuged at 28,000×g for 20 minutes, giving 453 ml of a supernatant.

(iii) The supernatant obtained in the above (ii) was dialyzed against 0.01M Tris.HCl buffer (pH 8.5) and then centrifuged at 19,000×g for 10 minutes. The supernatant thus obtained (458 ml) was applied to a DE52 (DEAE-cellulose, Whatman, Great Britain) column (50 ml in volume) equilibrated in advance with 0.01M Tris.HCl buffer (pH 8.5) to thereby effect protein adsorption. IL-2 was eluted by constructing a linear NaCl concentration gradient (0 to 0.15M NaCl, 1 liter). Active fractions (105 ml) were combined, concentrated to 10.2 ml using a YM-5 membrane (Amicon, U.S.A.) and subjected to gel filtration using a Sephacryl S-200 (Pharmacia, Sweden) column (500 ml in volume) equilibrated with 0.1M Tris.HCl (pH 8.0)-1M NaCl buffer. Active fractions (56 ml) were concentrated to 4.9 ml with a YM-5 membrane. The concentrate obtained was subjected to high performance liquid chromatography using an Ultrapore RPSC (Altex, U.S.A.) column and a tri-fluoroacetic acid-acetonitrile eluent system.

Column, Ultrapore RPSC (4.6×75 cm); column temperature, 30° C.; Eluent A, 0.1% trifluoroacetic acid-99.9% water; eluent B, 0.1% trifluoroacetic acid-99.9% acetonitrile; elution program, minute 0 (68% A+32% B)-minute 25 (55% A+45% B)-minute 35 (45% A+55% B)-minute 45 (30% A+70% B)-minute 48 (100% B); rate of elution, 0.8 ml/minute; detection wavelength, 230 nm. Active fractions exhibiting a retention time of about 39 minutes under the above conditions were collected and there was obtained 15 ml of a solution containing 7.5 mg of non-glycosylated human IL-2 protein [specific activity, 30,000 U/mg; activity recovery rate from starting material, 48.2%; purity of protein, 99% (as determined by densitometry)].

What is claimed is:

1. A human interleukin-2 composition in the form of a lyophilizate which comprises in addition to human interleukin-2, human serum albumin in a concentration of about 0.1 to 50 mg/ml as an aqueous solution, and, as a solution, is adjusted to have a pH between 3 to 6.

2. The composition according to claim 1, wherein the interleukin-2 is a recombinant interleukin-2.

3. The composition according to claim 1, wherein the human interleukin-2 is a non-glycosylated human interleukin-2.

4. The composition according to claim 1, wherein the interleukin-2 has a specific activity of 20,000 to 80,000 units/mg.

5. The composition according to claim 1, wherein the interleukin-2 is in a concentration of 1 to 80,000 units/ml as an aqueous solution.

6. The composition according to claim 1, which is free from a salt.

7. The composition according to claim 1, which comprises a combination of a human serum albumin and the reducing compound.

8. The composition according to claim 7, wherein the reducing compound is an acidic reducing compound.

9. The composition according to claim 8, wherein the acidic reducing compound is glutathione, thioctic acid, N-acetylcysteine, thioalkanoic acid of 1 to 7 carbon atoms or ascorbic acid.

10. The composition according to claim 7, wherein the reducing compound is in a concentration of 0.05–20 mg/ml as an aqueous solution.

11. The composition according to claim 1, which further comprises an monoamino aliphatic amino acid, a cyclic amino acid, a monosaccharide, a sugar alcohol or a combination thereof.

12. The composition according to claim 1, which further comprises monoamino aliphatic amino acid.

13. The composition according to claim 12, wherein the monoamino aliphatic amino acid is in a concentration of 5 to 50 mg/ml as an aqueous solution.

14. The composition according to claim 1, wherein the pH of the composition is adjusted by an acidic reducing compound, an acidic amino acid, a mineral acid or/and a buffer of organic acid.

15. The composition according to claim 1, wherein the pH is 3 to 5.5.

16. The composition according to claim 11, wherein the additional component is a monosaccharide, a sugar alcohol or a combination thereof in a concentration of 10 to 100 mg/ml.

* * * * *